United States Patent [19]

Trapasso

[11] 3,959,376

[45] May 25, 1976

[54] PRODUCTION OF 4-HALO-2-ALKENYL TRI-LOWER ALKYL AMMONIUM OR PHOSPHONIUM HALIDES

[75] Inventor: Louis E. Trapasso, Watchung, N.J.

[73] Assignee: Celanese Corporation, New York, N.Y.

[22] Filed: Jan. 28, 1974

[21] Appl. No.: 437,091

[52] U.S. Cl. ............... 260/567.6 M; 260/606.5 F
[51] Int. Cl.[2] ........................................ C07C 85/04
[58] Field of Search ............ 260/567.6 M, 567.6 R, 260/567.6 P, 606.5 F

[56] References Cited
UNITED STATES PATENTS

| | | |
|---|---|---|
| 3,557,214 | 1/1971 | Koenig et al. ............... 260/567.6 M |
| 3,689,468 | 9/1972 | Cenci et al. ..................... 260/86.1 N |

FOREIGN PATENTS OR APPLICATIONS

| | | | |
|---|---|---|---|
| 1,188,004 | 4/1970 | United Kingdom ......... 260/567.6 M |

OTHER PUBLICATIONS

Farmer et al., J. Chem. Soc. (1928), pp. 729–738.

*Primary Examiner*—James O. Thomas
*Assistant Examiner*—James H. Reamer

[57] ABSTRACT

The quaternary ammonium or phosphonium salts of halogenated lower alkene compounds such as 4-chloro-2-alkenyl trimethyl ammonium chloride are prepared by reacting a tri-lower alkyl amine or tri-lower alkyl phosphine with 3,4-dihaloalkene-1.

8 Claims, No Drawings

PRODUCTION OF 4-HALO-2-ALKENYL TRI-LOWER ALKYL AMMONIUM OR PHOSPHONIUM HALIDES

BACKGROUND OF THE INVENTION

The quaternary ammonium and phosphonium salts of halogenated alkene compounds such as 4-chloro-2-butenyl trimethyl ammonium or phosphonium chloride are useful as quaternizing agents in making cationic vinylic monomers useful in the production of polyacrylamides or other polymers that are currently used as flocculants. For example, in the following equation

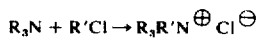

the R'Cl reactant functions as a quaternizing agent in converting the $R_3N$ into the quaternary salt $R_3R'N^\oplus Cl^\ominus$. Thus, cationic vinyl monomers may be produced as, for example, in the following equation

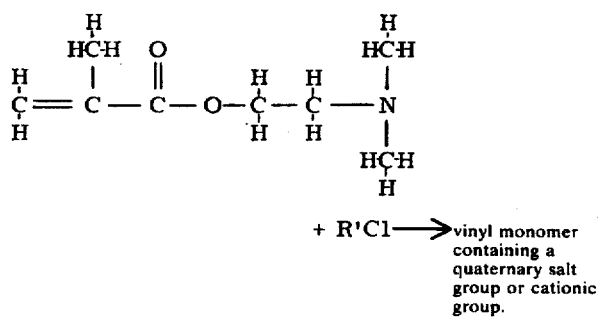

Such salts are also useful in the production of cationic starches and guar.

Compounds such as 4-halo-2-alkenyl tri-lower alkyl ammonium or phosphonium halide, and particular 4-chloro-2-butenty trimethyl ammonium or phosphonium chloride (both the cis and trans isomers), are of special interest as such quaternizing agents.

Processes for producing 4-chloro-2-butenyl trimethyl ammonium chloride are known in the art.

For example, in the past 4-chloro-2-butenyl trimethyl ammonium chloride has been prepared by reacting in solution 1,4-dichlorobutene-2 and trimethyl amine as illustrated in U.S. Pat. No. 3,689,468. Unfortunately, the use of 1,4-dichlorobutene-2 in this process is objectionable in that the 1,4-dichlorobutene-2 is not commercially available in sufficiently pure form. Thus, relatively expensive purification techniques must be performed on the commercially available 1,4-dichlorobutene-2 or the resulting 4-chloro-2-butenyl trimethyl ammonium chloride is also in relatively impure form and is unsuitable for use in the commercial production of cationic vinyl monomers. Also, commercially available 1,4-dichlorobutene-2 is relatively unstable and does not have a commercially acceptable shelf life (i,e., a shelf life of more than 1 year).

OBJECTS AND SUMMARY OF THE INVENTION

Accordingly, the general object of the present invention is to avoid or substantially alleviate the above problems with the prior art.

A more specific object is the provision of a process for the production of 4-halo-2-alkenyl tri-lower alkyl ammonium or phosphonium halides.

A further object is to provide an economical process for the production of relatively pure 4-halo-2-alkenyl tri-lower alkyl ammonium or phosphonium halides using relatively pure reactants.

Another object is to provide a process for the production of shelf-stable 4-halo-2-alkenyl tri-lower alkyl ammonium or phosphonium halides using relatively thermodynamically stable reactants.

Still another object is to provide a process for the production of 4-halo-2-alkenyl tri-lower alkyl ammonium or phosphonium halides such that the product formed is substantially the trans isomer.

Other objects and advantages of the present invention will become apparent from the following summary and description of the preferred embodiments of the present invention.

These and other objects are achieved by a process for producing 4-halo-2-alkenyl tri-lower alkyl ammonium of phosphonium halide which comprises reacting a tri-lower alkyl amine or a tri-lower alkyl phosphine with 3,4-dihaloalkene-1.

Analytical data (obtained through Nuclear Magnetic Resonance spectroscopy) indicate the surprising fact that the major product formed in the reaction of 3,4-dihaloalkene-1 with either a tri-lower alkyl amine or a tri-lower alkyl phosphine is the trans-4-halo-2-alkenyl tri-lower alkyl ammonium or phosphonium halide. By analogy with the reactions between (a) 1,4-dichlorobutene-2 and trimethyl amine, and (b) allyl chloride and trimethyl amine, it is expected that the reaction of 3,4-dichlorobutene-1 with either trimethyl amine or trimethyl phosphine would yield a product with a terminal double bond and amine or phosphine substitution on a secondary carbon atom. In fact, there is obtained a product with an internal double bond and amine or phosphine substitution on a primary carbon atom.

The following equations (a through c) illustrate the reaction between (a) 1,4-dichlorobutene-2 and trimethyl amine, (b) allyl chloride and trimethyl amine, and (c) 3,4-dichlorobutene-1 and trimethyl amine.

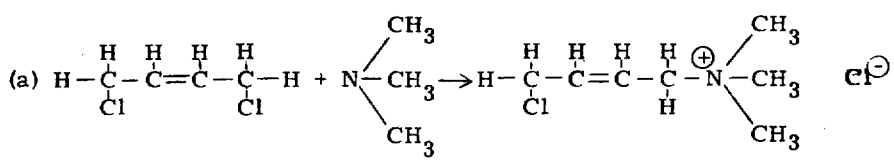

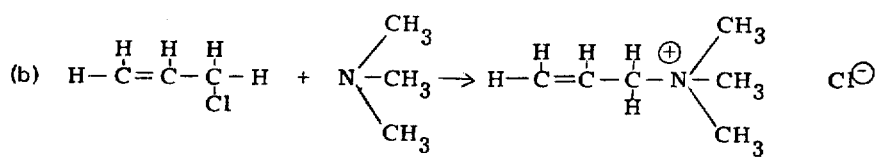

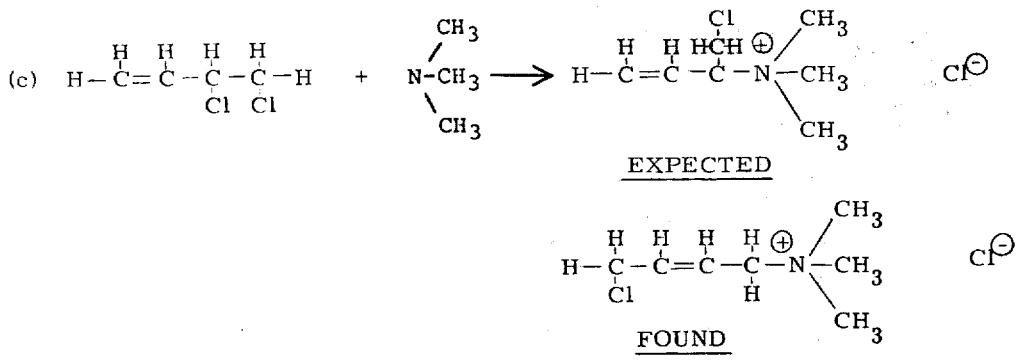

In reaction (a), a mixture of the cis and trans isomers of 1,4-dichlorobutene-2 is reacted with trimethyl amine to yield a mixture of the cis and trans isomers of 4-chloro-2-butenyl trimethyl ammonium chloride in the same cis/trans ratio as the starting materials. The reaction essentially replaces a terminal chlorine atom with a terminal trimethyl amino group. In reaction (b), a similar reaction mechanism is observed.

In reaction (c), however, the product obtained is different from that which would be expected. In addition, reaction (c) yields a product which is all trans isomer. Neither the cis isomer nor a product with a terminal double bond is detected as part of the product. The reaction product of trimethyl amine with 3,4-dichlorobutene is surprisingly the same as that which would be produced from the reaction of trans-1,4-dichlorobutene-2 with trimethyl amine.

The same result is obtained when trimethyl phosphine is reacted with 3,4-dichlorobutene-1.

DESCRIPTION OF THE PREFERRED EMBODIMENTS

The tri-lower alkyl amine or phosphine of the present process may be any amine or phosphine compound having three alkyl groups of from 1 to 8, typically from 1 up to 4, carbon atoms attached to a central nitrogen or phosphorus atom. The carbon atoms of the attached alkyl groups can be linked either in a straight or branched chain. The alkyl groups attached to the nitrogen or phosphorus atom can be the same or different.

Examples of particular tri-lower alkyl amine compounds useful in the present invention include triethyl amine, tri-n-butyl amine, and trimethyl amine. Trimethyl amine is particularly preferred.

Examples of particular tri-lower alkyl phosphine compounds useful in the present invention include triethyl phosphine, tri-n-butyl phosphine, and trimethyl phosphine. Trimethyl phosphine is particularly preferred.

The 3,4-dihaloalkene-1 of the present process includes any alkene reactant which has four or more carbon atoms in a straight chain and which has chlorine or bromine or any combination of two such halogens substituted in the 3 and 4 positions. Typical suitable alkene compounds include 3,4-dihalobutene-1, 3,4-dihalopentene-1, 3,4-halohexene-1, and 3,4-dihaloheptene-1. The dichloro derivative, i.e. 3,4-dichloroalkene-1 is preferred and 3,4-dichlorobutene-1 is particularly preferred.

The tri-lower alkyl amine or phosphine and 3,4-dihaloalkene-1 may be reacted in a compatible solvent such as a solvent in which the two reactants are soluble and the product is insoluble. Preferred solvents are the highly volatile organic solvents such as ketones, ethers, and aliphatic and aromatic hydrocarbons. Thus, suitable solvents include benzene, chlorohexane, tetrahydrofuran and acetone. A particularly preferred solvent is acetone.

Typically, the 3,4-dihaloalkene-1 is dissolved in a portion of solvent and the tri-lower alkyl amine or phosphine is dissolved in another portion of solvent and the two solutions are then mixed with stirring to form the 4-halo-2-alkenyl tri-lower alkyl ammonium or phosphonium halide product. When trimethyl amine or phosphine is the tri-lower alkyl amine or phosphine reactant, the staring materials may be reacted by first forming a solution of the 3,4-dihaloalkene-1, and then either bubbling the trimethyl amine or phosphine directly into the 3,4-dihaloalkene-1 solution or dissolving the trimethyl amine or phosphine in a solvent and then mixing this solution with the 3,4-dihaloalkene-1 solution.

The molar ratio of tri-lower alkyl amine or phosphine to 3,4-dihaloalkene-1 can vary widely but it may be generally from about 2:1 to about 0.5:1, typically from about 1.4:1 to about 0.8:1, and preferably from about 1.2:1 to about 0.95:1.

The present process may be carried out at subatmospheric, atmospheric, or superatmospheric pressures. Generally the process is performed at a pressure of from about 700 to about 1600 millimeters or more, typically from about 740 to about 1200 millimeters, and preferably from about 750 to about 900 millimeters or mercury.

The present process can be conducted over a wide temperature range. Of course, the temperature must be such that both reactants and solvents remain as a liquid or solution. The present process can be carried out generally at a temperature of from about −20° to about 80°C., typically from about 0° to about 50°C., and preferably from about 10° to about 30°C.

The reaction of the tri-lower alkyl amine or phosphine with 3,4-dihaloalkene-1 is relatively slow and the yield depends directly on the amount of time allowed for reaction. In order to maximize yield, the reactants should be in contact in solution generally for from about 3 to 60, typically from about 5 to about 48, preferably from about 6 to about 24 hours.

The 4-halo-2-alkenyl tri-lower alkyl ammonium or phosphonium halide product formed is a white solid, insoluble in acetone. This product is generally obtained in a yield of greater than about 75, typically greater than about 77 and preferably greater than about 80 percent by weight based on the theoretical yield of a product consisting of a one-to-one adduct of tri-lower alkyl amine or phosphine and 3,4-dihaloalkene-1.

The reaction product is a mixture of the trans-4-halo-2-alkenyl tri-lower alkyl ammonium or phosphonium halide, along with small amounts of the tri-lower alkyl amine or phosphine hydrochloride, and minor amounts of a di-quaternary salt and other impurities. The desired trans-4-halo-2-alkenyl tri-lower alkyl ammonium or phosphonium halide generally comprises at least about 65 percent, typically often at least about 70 percent by weight of the isolated product.

The present invention is further illustrated by the following Examples. All parts and percentages in the Examples as well as in the specification and claims are by weight unless otherwise specified. It should be understood, however, that the invention is not limited to the specific details of the Examples which are to be considered as illustrative of the present invention.

EXAMPLE I

This Example illustrates the preparation of 4-chloro-2-butenyl trimethyl ammonium chloride.

74.5 grams of 3,4-dichlorobutene-1 is dissolved in 0.3 liters of acetone in a one liter vessel with the aid of a mechanical stirrer. 42.19 grams of trimethyl amine gas (i.e., a 1.2:1 molar ratio of 3,4-dichlorobutene-1 to trimethyl amine) in acetone is bubbled directly into this solution while the reaction medium is maintained at 25°C. and atmospheric pressure (760 mm. mercury). A white solid begins to precipitate from the solution. The solution is reacted with stirring for 8 hours.

After eight hours, the white precipitate is filtered on a Buchner funnel, and dried in a vacuum oven at 45°C. for about 12 hours.

The total yield of dry solid is 82 percent of theory. Nuclear Magnetic Resonance (NMR) analysis indicates that 70 percent of the recovered solid is trans-chloro-2-butenyl trimethyl ammonium chloride. No terminal double bond is detected in the product and no cis structure is present. Substantially all of the remaining impurities is trimethyl amine hydrochloride which does not interfere or otherwise detrimentally affect the use of the product as a quaternizing agent in making cationic vinyl monomers.

EXAMPLE II

This Example illustrates the preparation of 4-chloro-2-butenyl trimethyl phosphonium chloride.

In this Example the same procedure is used as in Example 1 except that 45.6 grams of trimethyl phosphine are used instead of the 42.19 grams of trimethyl amine (1.2:1 molar ratio of trimethyl phosphine to 3,4-dichlorobutene-1).

The product is a white solid insoluble in acetone. The total yield of dry solids is 80 percent of theory. NMR analysis indicates that the product is 70 percent 4-chloro-2-butenyl trimethyl phosphonium chloride with trimethyl phosphonium hydrochloride being the main impurity. No terminal bond is detected in the product and no cis structure is present.

As hereinabove stated, trans-4-halo-2-alkenyl tri-lower alkyl ammonium or phosphonium chlorides are useful as quaternizing agents in making cationic vinyl monomers useful in the production of polyacrylamides or other polymers that are currently used as flocculants. These compounds are also useful in the production of cationic starches and guar.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A process for producing 4-chloro-2-alkenyl tri-lower alkyl ammonium or phosphonium chloride which comprises reacting a 3,4-dichloroalkene-1 with a tri-lower alkyl amine or tri-lower alkyl phosphine, in a molar ratio of tri-lower alkyl amine or phosphine to 3,4-dichloroalkene-1 of about 2:1 to about 0.5:1, in a solvent at a temperature of from about 0°C to about 50°C for a period of time sufficient to yield the desired product.

2. The process of claim 1 wherein the 3,4-dichloroalkene-1 is reacted with trimethyl amine.

3. The process of claim 2 wherein 3,4-dichloroalkene-1 is 3,4-dichlorobutene-1.

4. The process of claim 3 wherein the reaction is carried out in acetone.

5. The process of claim 1 wherein the 3,4-dichloroalkene-1 is reacted with trimethyl phosphine.

6. A process for producing 4-chloro-2-butenyl trimethyl ammonium or phosphonium chloride which comprises reacting 3,4-dichlorobutene-1 with trimethyl amine or trimethyl phosphine, in a molar ratio of trimethyl amine or phosphine to 3,4-dichlorobutene-1 of about 2:1 to about 0.5:1 in a solvent at a temperature of from about 0°C to about 50°C, for a period of time sufficient to yield the desired product.

7. The process of claim 6 wherein the molar ratio of trimethyl amine or phosphine to 3,4-dichlorobutene-1 is from about 1.4:1 to about 0.8:1.

8. A process for preparing 4-chloro-2-butenyl trimethyl ammonium or phosphonium chloride which comprises reacting trimethyl amine or trimethyl phosphine with 3,4-dichlorobutene-1 in acetone at a temperature of from about 10° to about 30°C. and at a pressure of from about 750 to about 900 millimeters of mercury, the molar ratio of trimethyl amine or trimethyl phosphine to 3,4-dichlorobutene-1 being from about 1.2:1 to about 0.95:1.

* * * * *